United States Patent
Paborji

(10) Patent No.: US 8,470,864 B2
(45) Date of Patent: *Jun. 25, 2013

(54) COMPOSITIONS AND METHODS FOR THE TREATMENT OF OVERACTIVE BLADDER

(75) Inventor: Mehdi Paborji, Cupertino, CA (US)

(73) Assignee: Theravida, Inc., Mountain View, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/710,301

(22) Filed: Feb. 22, 2010

(65) Prior Publication Data
US 2010/0152263 A1 Jun. 17, 2010

Related U.S. Application Data

(63) Continuation of application No. 12/555,806, filed on Sep. 8, 2009, now Pat. No. 7,666,894, which is a continuation of application No. 11/467,760, filed on Aug. 28, 2006, now Pat. No. 7,678,821.

(60) Provisional application No. 60/714,150, filed on Sep. 2, 2005.

(51) Int. Cl.
- A61K 31/00 (2006.01)
- A61K 31/137 (2006.01)
- A61K 31/216 (2006.01)
- A61K 31/46 (2006.01)

(52) U.S. Cl.
USPC .............. 514/397; 514/534; 514/648

(58) Field of Classification Search
USPC .......................... 514/397, 534, 648
See application file for complete search history.

(56) References Cited

U.S. PATENT DOCUMENTS

| | | | |
|---|---|---|---|
| 6,482,837 B1 | 11/2002 | Wood | |
| 6,627,635 B2 | 9/2003 | Palermo et al. | |
| 6,716,449 B2 | 4/2004 | Oshlack et al. | |
| 7,026,329 B2 | 4/2006 | Crain et al. | |
| 7,419,686 B2 | 9/2008 | Kaiko | |
| 7,666,894 B2 * | 2/2010 | Paborji | 514/397 |
| 7,678,821 B2 * | 3/2010 | Paborji | 514/397 |
| 7,781,472 B2 * | 8/2010 | Paborji | 514/397 |

FOREIGN PATENT DOCUMENTS
WO 97/09980 3/1997

OTHER PUBLICATIONS

Wall et al., Pharmacotherapy, 22(5), (2002), pp. 621-629.*
Chancellor, Michael B. et al., "A Comparison of the Effects on Saliva Output of Oxybutynin Chloride and Tolterodine Tartrate," Clinical Therapeutics, (2001) 23:5:753-760.*
Oki et al., Journal of Urology, (Nov. 2004), 172(5), pp. 2059-2064.*
Aframian, D.J. et al., "Pilocarpine Treatment in a Mixed Cohort of Xerostomic Patients," Oral Diseases, (2007) 13:88-92.

(Continued)

*Primary Examiner* — Savitha Rao
(74) *Attorney, Agent, or Firm* — Sam K. Tahmassebi; TechLaw LLP

(57) ABSTRACT

Disclosed herein are pharmaceutical compositions comprising oxybutynin or tolterodine, or a free base thereof or a pharmaceutically acceptable salt thereof, and pilocarpine, or a free base thereof or a pharmaceutically acceptable salt thereof. Also disclosed are methods of treating a patient suffering from overactive bladder comprising administering to the patient the above pharmaceutical composition.

11 Claims, 7 Drawing Sheets

OTHER PUBLICATIONS

Aromdee, Chantana et al., "A Pilot Study of the Disposition of Pilocarpine in Plasma, Saliva and Urine After a Single Oral Dose," European Journal of Pharmaceutical Sciences, (1999) 8:81-83.

Chapple, Christopher et al., "The Effects of Antimuscarinic Treatments in Overactive Bladder: A Systematic Review and Meta-Analysis," European Urology, (2005) 48:5-26.

Diokno, Ananias et al., "Prospective, Randomized, Double-Blind Study of the Efficacy and Tolerability of the Extended-Release Formulations of Oxybutynin and Tolterodine for Overactive Bladder: Results of the OPERA Trial," Mayo Clin Proc., (2003) 78:687-695.

Foote, Jenelle et al., "Treatment of Overactive Bladder in the Older Patient: Pooled Analysis of Three Phase II Studies of Darifenacin, an M3 Selective Receptor Antagonist," European Urology, (2005) 48:471-477.

MacDiarmid, Scott A. et al., "Efficacy and Safety of Extended Release Oxybutynin for the Treatment of Urge Incontinence: An Analysis of Data From 3 Flexible Dosing Studies," The Journal of Urology, (2005) 174:1301-1305.

Oki, Tomomi et al., "Comparitive Evaluation of Exocrine Muscarinic Receptor Binding Characteristics and Inhibition of Salivation of Solifenacin in Mice," Biol. Pharm. Bull, (2006) 29(7)1 397-1400.

Oki, Tomomi et al., "Muscarinic Receptor Binding, Plasma Concentration and Inhibition of Salivation After Oral Administration of a Novel Antimuscarinic Agent, Solifenacin Succinate in Mice," British Journal of Pharmacology, (2005) 145:219-227.

Serra, Denise B. et al., "QT and QTc Interval with Standard and Supratherapeutic Doses of Darifenacin, a Muscarinic M3 Selective Receptor Antagonist for the Treatment of Overactive Bladder," Journal Clinical Pharmacology, (2005) 45:1038-1047.

Siami, Paul et al., "A Multicenter, Prospective, Open-Label Study of Tolterodine Extended-Release 4 mg for Overactive Bladder: The Speed of Onset of Therapeutic Assessment Trial (STAT)," Clinical Therapeutics, (2002) 24:616-628.

Smulders, Ronald A. et al., "Pharmacokinetics and Safety of Solinfenacin Succinate in Healthy Young Men," Journal of Clinical Pharmacology, (2004) 44:1023-1033.

Steers, William et al., "An Investigation of Dose Titration with Darifenacin, an Mx-Selective Receptor Antagonist," BJU International (2005) 95:580-586.

Tiwari, Atul and Krishna S. Naruganahalli, "Current and Emerging Investigational Medical Therapies for the Treatment of Overactive Bladder," Expert Opin. Investig. Drugs, (2006) 15(9):1017-1037.

Versi, Eboo et al., "Dry Mouth with Conventional and Controlled-Releases Oxybutynin in Urinary Incontinence," Obstetrics & Gynecology, (2000) 95:718-721.

Waldeck, Kristian et al., "Comparison of Oxybutynin and its Active Metabolite, N-Desethyl-Oxybutynin, in the Human Detrusor and Parotid Gland," The Journal of Urology, (1997) 157:1093-1097.

Zinner, Norman et al., "Trospium Chloride Improves Overative Bladder Symptoms: A Multicenter Phase III Trial," Journal of Urology, (2004) 171:2311-2315.

Salah, R.S. et al., "Pilocarpine for Anticholinergic Adverse Effects Asscoaited with Desipramine Treatement [6]," American Journal of Psychiatry, (1996) 153:579.

Masters, Kim J., "Pilocarpine Treatement of Xerostmia Induced by Psychoactive Medications," American Journal of Psychiatry, (2005) 162:1023.

International Preliminary Report on Patentability issued Apr. 16, 2007 in PCT/US2006/033671.

Harris, N. O. et al., "Infrared Spectral Characteristics of Pilocarpine-stimulated Saliva of Normally Caries-resistant Animals Compared with Caries-resistant and -susceptible Humans," J. Dent. Res. 1960, 39, 810.

Yakushiji, T. et al., "Effects of Benzodiazepines and Non-benzodiazepine Compounds on the GABA-induced Response in Frog Isolated Sensory Neurones," Br. J. Pharmacol. 1989, 98, 735-40.

Löscher, W. and Hönack, D., "Withdrawal Precipitation by Benzodiazepine Receptor Antagonists in Dogs Chronically Treated with Diazepam or the Novel Anxiolytic and Anticonvulsant Beta-carboline Abecarnil," Naunyn Schmiedebergs Arch. Pharmacol. 1992, 345, 452-60.

Oki, Tomomi et al., "Demonstration of Bladder Selective Muscarinic Receptor Binding by Intravesical Oxybutynin to Treat Overactive Bladder," The Journal of Urology 2004, 172, 2059-2064.

Bob A. Rappaport, NDA Approval letter for EMBEDA(TM), Aug. 13, 2009.

Prescribing information for EMBEDA(TM), 2009.

Prescribing information for DETROL(TM), 2009.

ChristopHer R. Chapple, "Muscarinic Receptor Antagonists in the Treatment of Overactive Bladder," Urology, 55 (Supplement 5A), May 2000, 33-46.

* cited by examiner

COMPOSITIONS AND METHODS FOR THE TREATMENT OF OVERACTIVE BLADDER

RELATED APPLICATION

This application is a continuation of U.S. application Ser. No. 12/555,806, filed, Sep. 8, 2009, by Mehdi Paborji, and entitled "THERAPY FOR THE TREATMENT OF DISEASE," now U.S. Pat. No. 7,666,894, issued on Feb. 23, 2010, which in turn is a continuation of U.S. application Ser. No. 11/467,760, filed, Aug. 28, 2006, by Mehdi Paborji, and entitled "THERAPY FOR THE TREATMENT OF DISEASE," which in turn claims priority to U.S. Provisional Application No. 60/714,150, filed Sep. 2, 2005, by Mehdi Paborji, and entitled "THERAPY FOR THE TREATMENT OF DISEASE," the entire disclosure, including the drawings, of all of which are incorporated herein by reference.

BACKGROUND OF THE INVENTION

1. Field of the Invention

The present invention is in the field of pharmaceutical compositions and methods of using the same for the treatment of overactive bladder and reduction of various side effects thereof.

2. Description of the Related Art

Overactive bladder (OAB) is characterized by involuntary contractions of the detrusor muscle during bladder filling. These contractions may be asymptomatic or may cause the three common symptoms that clinically define OAB: frequency of urination; urgency; and urge, or reflex, incontinence. Frequency is an increase in the number of micturitions, to as many as eight or more a day. Urgency is the strong and sudden desire to urinate. Urge incontinence, or reflex incontinence, is the situation where the urge to urinate cannot be controlled. Nocturia, or nighttime urinary frequency that disturbs sleep (more than twice a night), is often included as a fourth symptom. The symptoms of OAB may appear individually or together, and it is not known whether they have a pathologic or neurogenic cause.

Incontinence is present in over half of female patients with OAB. This condition affects more than 33 million Americans and imposes considerable economic, social, and psychological burdens. Although continued research in the pharmacologic management of lower urinary tract disorders have led to alternative treatment options, the symptoms of OAB are generally underreported by patients and under-treated by healthcare professionals.

Several classes of medications have been used to treat and manage OAB, including calcium channel blockers, tricyclic antidepressants, alpha-adrenergic antagonists, estrogen, and anticholinergic agents. Anticholinergic agents, which exert their effects at muscarinic receptors and suppress or diminish the intensity of involuntary detrusor muscle contractions, are the first-choice pharmacotherapy for OAB, and may be the only therapy available whose efficacy is not in question. Oxybutynin chloride and tolterodine tartrate are the most extensively studied of the anticholinergic agents, and the most widely used. A recent evidence-based systematic review of controlled clinical trials of several agents concluded that anticholinergic therapies significantly improved several indices of lower urinary tract function, including frequency of micturition and number of incontinence episodes. A major limitation of these agents is that they lack specificity for bladder tissue, with resultant bothersome side effects such as dry mouth and constipation.

Tolterodine has generally been associated with less dry mouth than oxybutynin. This property is thought to be due to the decreased selectivity of tolterodine for any one of the 5 muscarinic receptor subtypes (M1-M5), such as the M3 receptor that predominates in parotid tissue. Oxybutynin, more than tolterodine, has a high affinity for this receptor, which also mediates bladder contraction. It has been argued on the basis of animal data that tolterodine has a greater selectivity than oxybutynin for bladder than for parotid muscarinic receptors, but such a mechanism remains to be elucidated. Effects on M2 receptors, which populate bladder smooth muscle though not glandular tissue, and for which tolterodine shows a greater affinity than oxybutynin, have also been invoked to explain the relatively slightly lower degree of dry mouth that is associated with the therapeutic effect of tolterodine.

Additional reports that the higher extent of dry mouth with oxybutynin is attributed to formation of the major metabolite, desethyloxybutynin, which appears to have a greater affinity for the M3 subtype receptors also expressed in the salivary glands. However, the newer extended-release formulations of oxybutynin and tolterodine provide comparable or perhaps slightly better efficacy and enhanced tolerability compared with immediate-release formulations. More recently approved agents including trospium chloride, solifenacin succinate (Vesicare) and darifenacin (Enablex) appear to have a better side effect profile, i.e., slightly less dry mouth. Nonetheless, the dry mouth and constipation continue to be problematic and patients stop taking the medication after short period of therapy.

Thus, there exists a need in the art for a medication that provides sufficient efficacy for the treatment of OAB, with much reduced level of side effects in order to increase patient compliance, comfort, and efficacy.

SUMMARY OF THE INVENTION

Disclosed herein are pharmaceutical compositions comprising a therapeutically effective amount of a first compound and a therapeutically effective amount of a second compound, wherein the first compound is an antimuscarinic or an anticholinergic agent and the second compound causes stimulation of salivary glands. Also, disclosed herein are pharmaceutical compositions comprising a therapeutically effective amount of a first compound and a therapeutically effective amount of a second compound, wherein the first compound is an antimuscarinic or an anticholinergic agent and the second compound relieves constipation. Further, disclosed herein are pharmaceutical compositions comprising a therapeutically effective amount of a first compound, a therapeutically effective amount of a second compound, and a therapeutically effective amount of a third compound, wherein the first compound is an antimuscarinic or an anticholinergic agent, the second compound causes stimulation of salivary glands, and the third compound relieves constipation.

Disclosed herein are methods of treating a patient comprising administering to a patient in need thereof a therapeutically effective amount of a first compound and a therapeutically effective amount of a second compound, wherein the first compound is an antimuscarinic or an anticholinergic agent and the second compound causes stimulation of salivary glands. Also disclosed herein are methods of treating a patient comprising administering to a patient in need thereof a therapeutically effective amount of a first compound and a therapeutically effective amount of a second compound, wherein the first compound is an antimuscarinic or an anticholinergic agent and the second compound causes stimulation of salivary glands. Further, disclosed herein are methods of treating a patient comprising administering to a patient in need thereof a therapeutically effective amount of a first compound, a therapeutically effective amount of a second compound, and a therapeutically effective amount of a third compound, wherein the first compound is an antimuscarinic or an anticholinergic agent, the second compound causes stimulation of salivary glands, and the third compound relieves constipation.

DETAILED DESCRIPTION OF THE PREFERRED EMBODIMENTS

Figure 1:
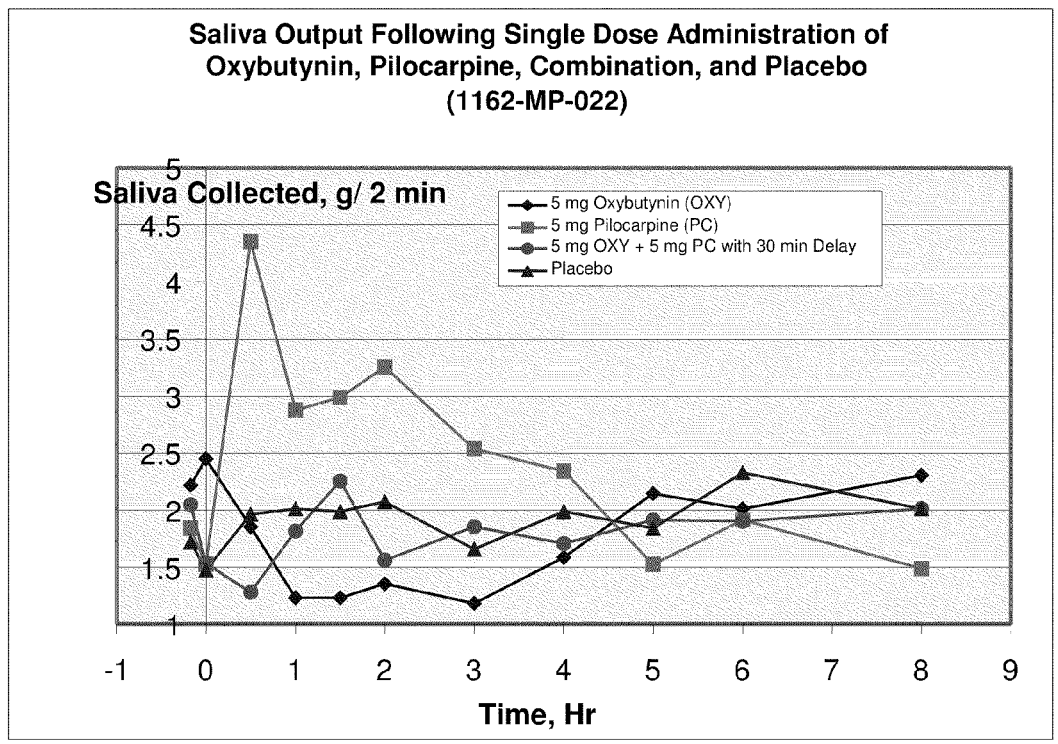
FIG. 1 is a graph showing the amount of saliva flow collected in a human subject subsequent to the administration of oxybutynin (♦, diamond), pilocarpine (■, square), both (●, circle), and neither (▲, triangle).

The major limitations of treatment of overactive bladder (OAB) are the dry mouth and constipation side effects. The current approach to address the dry mouth is development of sustained release of the active moiety, such as oxybutynin or tolterodine. Patients taking OAB medications still suffer from these side effects and thus their quality of life is hampered significantly to the extend that majority of patients discontinue the mediations after about 4-6 months.

Thus, in the first aspect, the present invention relates to a pharmaceutical composition comprising a therapeutically effective amount of a first compound and a therapeutically effective amount of a second compound, wherein the first compound is an antimuscarinic or an anticholinergic agent and the second compound causes stimulation of salivary glands.

The first compound of the pharmaceutical compositions described herein is a compound useful in the treatment of overactive bladder. In some embodiments, the first compound is an agonist of M2 or M3 muscarinic receptors. In further embodiments, the first compound may be selected from the group consisting of oxybutynin, tolterodine, solifenacin, darifenacin, trospium, fesoterodine, or a pharmaceutically acceptable salt or prodrug thereof. Other compounds known now or later developed for the treatment of OAB are within the scope of the present disclosure.

In some embodiments, the first compound is a compound of Formula I

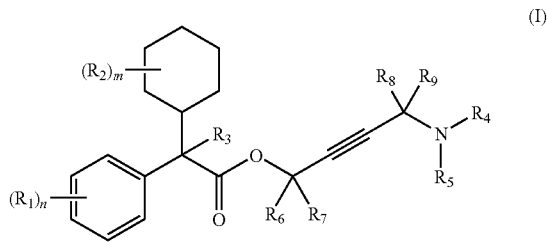

(I)

or a pharmaceutically acceptable salt or prodrug thereof, wherein:

$R_1$-$R_9$ are each independently selected from the group consisting of hydrogen, alkyl, nitro, amino, cyano, hydroxy, alkoxy, carboxylate, and amide; and m and n are each independently selected from 1, 2, 3, 4, and 5.

In some embodiments, each $R_1$ and $R_2$ is independently selected from the group consisting of hydrogen, alkyl, hydroxy, and alkoxy. In certain embodiments, each $R_1$ and $R_2$ is hydrogen.

In some embodiments, $R_3$ is selected from the group consisting of hydrogen, alkyl, hydroxy, and alkoxy. In certain embodiments, $R_3$ is hydroxy.

In some embodiments, $R_4$ and $R_5$ are each independently selected from the group consisting of hydrogen, alkyl, hydroxy, and alkoxy. In certain embodiments, $R_4$ and $R_5$ are each independently an alkyl. In further embodiments, $R_4$ and $R_5$ are each independently selected from the group consisting of methyl, ethyl, propyl, n-butyl, isobutyl, and tert-butyl. In other embodiments, $R_4$ and $R_5$ are each independently ethyl.

In some embodiments, $R_6$-$R_9$ are each independently selected from the group consisting of hydrogen, alkyl, hydroxy, and alkoxy. In certain embodiments, $R_6$-$R_9$ are each independently a hydrogen.

In some embodiments, the first compound is oxybutynin, or a pharmaceutically acceptable salt or prodrug thereof. Oxybutynin is the active ingredient found in drugs such as Ditropan®; Ditropan XL®; and Oxytrol®. Oxybutynin is an anticholinergic drug, thereby suppressing involuntary contractions of the bladder's smooth muscle. Oxybutynin is also believed to have muscarinic receptor activity, which further enhances its OAB efficacy, but also may be the reason behind its most prevalent side effect, dry mouth.

In some embodiments, the first compound is tolterodine, or a pharmaceutically acceptable salt or prodrug thereof. Tolterodine, which has the chemical name (R)-2-[3-[bis(1-methylethyl-amino]-1-phenylpropyl]-4-methylphenol [R—(R*,R*)]-2,3-dihydroxybutanedioic acid, is a muscarinic receptor antagonist and is the active ingredient found in drugs such as Detrol® (as tolterodine tartrate). In another embodiment, the first compound is the 5-hydroxymethyl derivative of tolterodine.

The term "pharmaceutically acceptable salt" refers to a formulation of a compound that does not cause significant irritation to an organism to which it is administered and does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, succinic acid, tartaric acid, methanesulfonic acid, ethanesulfonic acid, p-toluenesulfonic acid, salicylic acid and the like. Pharmaceutical salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts thereof with amino acids such as arginine, lysine, and the like.

Throughout the present disclosure, when a particular compound is named, it is understood that the name refers to both the free base, or free acid, of the compound, and the pharmaceutically acceptable salts thereof. Thus, for example, the scope of the term "tolterodine" covers both the free base of tolterodine, i.e., (R)-2-[3-[bis(1-methylethyl-amino]-1-phenylpropyl]-4-methylphenol [R—(R*,R*)]-2,3-dihydroxybutanedionic acid, and its various pharmaceutically acceptable salts, for example tolterodine tartrate.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to provide the active moiety.

In some embodiments, the second compound is a cholinergic agonist. In certain embodiments, the second compound is selected from the group consisting of pilocarpine, cevimeline, and amifostine (the latter agent known chemically as 2-[(3-aminopropyl)amino]ethanethiol dihydrogen phosphate (ester)), or a pharmaceutically acceptable salt or prodrug thereof. In further embodiments, the second compound is pilocarpine, or a pharmaceutically acceptable salt or prodrug thereof. In other embodiments, the second compound is cevimeline, or a pharmaceutically acceptable salt or prodrug thereof.

In some embodiments, the second compound is a compound of Formula II

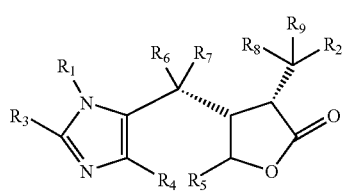

(II)

or a pharmaceutically acceptable salt or prodrug thereof, wherein $R_1$-$R_9$ are each independently selected from the group consisting of hydrogen, alkyl, nitro, amino, cyano, hydroxy, alkoxy, carboxylate, and amide.

In some embodiments, $R_1$ and $R_2$ are each independently selected from the group consisting of hydrogen, alkyl, hydroxy, and alkoxy. In certain embodiments, $R_1$ and $R_2$ are each independently an alkyl. In further embodiments, $R_1$ and $R_2$ are each independently selected from the group consisting of methyl, ethyl, propyl, n-butyl, isobutyl, and tert-butyl. In other embodiments, $R_1$ and $R_2$ are each independently methyl.

In some embodiments, $R_3$-$R_9$ are each independently selected from the group consisting of hydrogen, alkyl, hydroxy, and alkoxy. In certain embodiments, $R_3$-$R_9$ are each independently a hydrogen.

In another aspect, the present invention relates to a pharmaceutical composition comprising a therapeutically effective amount of a first compound and a therapeutically effective amount of a second compound, wherein the first compound is an antimuscarinic or an anticholinergic agent, as described above, and the second compound relieves constipation.

In certain embodiments, the second compound is selected from the group consisting of a stool softener, a laxative, a fiber treatment, and a $5HT_4$ receptor partial agonist. In some embodiments, the second compound is selected from the group consisting of bisacodyl, carboxymethylcellulose, casanthranol, cascara sagrada, castor oil, danthron, dehydrocholic acid, docusate calcium, docusate sodium, glycerin, lactulose, magnesium citrate, magnesium hydroxide, magnesium oxide, magnesium sulfate, malt soup extract, methylcellulose, milk of magnesia, mineral oil, mucilloid, polycarbophil, polyethylene glycol 3350, poloxamer 188, psyllium, psyllium hydrophilic, senna, sennosides, and sodium phosphate.

In certain embodiments, the second compound is a compound of Formula III

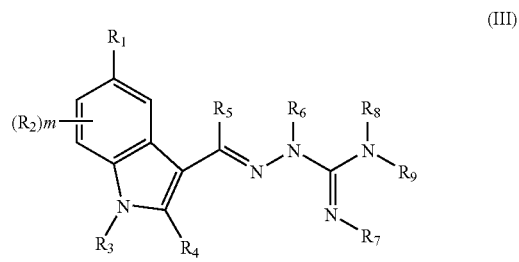

(III)

or a pharmaceutically acceptable salt or prodrug thereof, wherein $R_1$-$R_9$ are each independently selected from the group consisting of hydrogen, alkyl, nitro, amino, cyano, hydroxy, alkoxy, carboxylate, and amide, and m is selected from 1, 2, and 3.

In some embodiments, $R_1$ is selected from the group consisting of hydrogen, alkyl, hydroxy, and alkoxy. In certain embodiments, $R_1$ is a hydroxy or an alkoxy. In further embodiments, $R_1$ is selected from the group consisting of hydroxy, methoxy, ethoxy, propoxy, n-butoxy, isobutoxy, and tert-butoxy. In other embodiments, $R_1$ is methoxy.

In some embodiments, each $R_2$ and $R_3$-$R_9$ are each independently selected from the group consisting of hydrogen, alkyl, hydroxy, and alkoxy. In certain embodiments, each $R_2$ and $R_3$-$R_9$ are each independently a hydrogen.

In some embodiments, $R_9$ is selected from the group consisting of hydrogen, alkyl, hydroxy, and alkoxy. In certain embodiments, $R_9$ is an alkyl. In further embodiments, $R_9$ is selected from the group consisting of methyl, ethyl, propyl, n-butyl, isobutyl, tert-butyl, pentyl, hexyl, heptyl, and octyl. In other embodiments, $R_9$ is n-pentyl.

In certain embodiments, the second compound is tegaserod, or a pharmaceutically acceptable salt or prodrug thereof. In some of these embodiments, the pharmaceutically acceptable salt of tegaserod is selected from the group consisting of the nitrate, lactate, succinate, sulphate, mesylate, esylate, and hydrogen sulfate salts. However, other salts of tegaserod are also within the scope of the present invention.

Throughout the present disclosure, when a particular compound is mentioned by name, for example, oxybutynin, tolterodine, pilocarpine, cevimeline, or tegaserod, it is understood that the scope of the present disclosure encompasses pharmaceutically acceptable salts, esters, amides, or prodrugs of the named compound. Also, if the named compound comprises a chiral center, the scope of the present disclosure also includes compositions comprising the racemic mixture of the two enantiomers, as well as compositions comprising each enantiomer individually substantially free of the other enantiomer. Thus, for example, contemplated herein is a composition comprising the S enantiomer substantially free of the R enantiomer, or a composition comprising the R enantiomer substantially free of the S enantiomer. By "substantially free" it is meant that the composition comprises less than 10%, or less than 8%, or less than 5%, or less than 3%, or less than 1% of the minor enantiomer. If the named compound comprises more than one chiral center, the scope of the present disclosure also includes compositions comprising a mixture of the various diastereomers, as well as compositions comprising each diastereomer substantially free of the other diastereomers. Thus, for example, commercially available oxybutynin is a racemic mixture comprising two separate enantiomers. The recitation of "oxybutynin" throughout this disclosure includes compositions that comprise the racemic mixture of oxybutynin, the compositions that comprise the (+) enantiomer substantially free of the (−) enantiomer, and the compositions that comprise the (−) enantiomer substantially free of the (+) enantiomer. Further, for example, commercially available pilocarpine, which is a naturally occurring alkaloid, comprises two stereocenters. The scope of the present invention includes pharmaceutical compositions comprising all four diastereomers, pharmaceutical compositions comprising the racemic mixture of R,R and S,S isomers, pharmaceutical compositions comprising the racemic mixture of R,S and S,R isomers, pharmaceutical compositions comprising the R,R enantiomer substantially free of the other diastereomers, pharmaceutical compositions comprising the S,S enantiomer substantially free of the other diastereomers, pharmaceutical compositions comprising the R,S enantiomer substantially free of the other diastereomers, and pharmaceutical compositions comprising the S,R enantiomer substantially free of the other diastereomers.

In yet another aspect, the present invention relates to a pharmaceutical composition comprising a therapeutically effective amount of a first compound, a therapeutically effective amount of a second compound, and a therapeutically effective amount of a third compound, wherein the first compound is an antimuscarinic or an anticholinergic agent, as described above, the second compound causes stimulation of salivary glands, as described above, and the third compound relieves constipation, as described above.

In certain embodiments, the present invention relates to a pharmaceutical composition comprising oxybutynin and pilocarpine. In other embodiments, the present invention relates to a pharmaceutical composition comprising tolterodine and pilocarpine. In yet other embodiments, the present invention relates to a pharmaceutical composition comprising trospium and pilocarpine. In some embodiments, the present invention relates to a pharmaceutical composition comprising solifenacin and pilocarpine. In further embodiments, the present invention relates to a pharmaceutical composition comprising darifenacin and pilocarpine. In yet other embodiments, the present invention relates to a pharmaceutical composition comprising fesoterodine and pilocarpine. In other embodiments, ments, the present invention relates to a pharmaceutical composition comprising oxybutynin and cevimeline. In other embodiments, the present invention relates to a pharmaceutical composition comprising tolterodine and cevimeline.

In certain embodiments disclosed herein, an individual is given a pharmaceutical composition comprising a combination of two or more compounds to treat overactive bladder. In some of these embodiments, each compound is a separate chemical entity. However, in other embodiments, the two compounds are joined together by a chemical linkage, such as a covalent bond, so that the two different compounds form separate parts of the same molecule. The chemical linkage is selected such that after entry into the body, the linkage is broken, such as by enzymatic action, acid hydrolysis, base hydrolysis, or the like, and the two separate compounds are then formed.

In other embodiments, the chemical linkage is selected such that it is not broken under physiological conditions and is impervious to enzymatic attack. In these embodiments, the two parts of the compound remain intact in the patient's body. By "not broken" and "impervious" it is meant that the half-life of the chemical reaction leading to the breaking of the bond between the two parts of the molecule is longer than the pharmacological half-life of the joint compound, that is, the joint compound is excreted or metabolized faster than the bond between the two parts is broken.

Thus, in another aspect, the present invention relates to synthetic routes to novel molecules in which oxybutynin, tolterodine, trospium, solifenacin, and darifenacin is linked by a flexible linker to a pilocarpine moiety or other salivary gland stimulants.

The compounds useful for the compositions and methods described herein may be used in various formulations. Certain formulations affect the rate at which the compound enters the blood stream of the patient. Thus, some formulations are immediate release formulations while other formulations are delayed release, sustained release, or extended release formulations.

Thus, in some embodiments, the first compound is in immediate formulation, while in other embodiments the first compound is in delayed release formulation, and in yet other embodiments the first compound is in sustained release formulation, and in further embodiments the first compound is in extended release formulation. In some embodiments, the second compound is in immediate release formulation, while in other embodiments the second compound is in delayed release formulation, and in yet other embodiments the second compound is in sustained release formulation, and in further embodiments the second compound is in extended release formulation. In some embodiments, the third compound is in immediate release formulation, while in other embodiments the third compound is in delayed release formulation, and in yet other embodiments the third compound is in sustained release formulation, and in further embodiments the third compound is in extended release formulation.

The compositions described herein are particularly useful in alleviating the major side effects in the treatment of OAB, namely dry mouth and/or constipation, improving tolerability, and enhancing patient compliance while increasing the patient's quality of life.

In another aspect, the present invention relates to a method of treating a patient comprising administering to a patient in need thereof a therapeutically effective amount of a first compound and a therapeutically effective amount of a second compound, wherein the first compound is an antimuscarinic or an anticholinergic agent, as described above, and the second compound causes stimulation of salivary glands, as described above.

A patient in need of the treatment methods disclosed herein may be a patient who suffers from overactive bladder. The patient may also be one who finds current therapies for overactive bladder uncomfortable and/or the side effects of the therapy, such as the dry mouth or constipation, intolerable enough so as to require adjunct therapy to alleviate the side effects. The patient may also be one who is considering discontinuing therapy for overactive bladder due to the side effects of the therapy. In some embodiments, a patient who is recently diagnosed with overactive bladder but yet has not been treated therefore is a patient in need of the treatment methods and compositions disclosed herein. In these embodiments, the patient begins the therapy using the methods and combinations disclosed herein so that the patient does not experience any of the side effects, or experience the side effects to a lesser degree.

In some embodiments, the patient may be suffering from overactive bladder, urge, stress, and mixed incontinence.

In some embodiments the first compound and the second compound are administered more or less simultaneously. In other embodiments the first compound is administered prior to the second compound. In yet other embodiments, the first compound is administered subsequent to the second compound.

In another aspect, the present invention relates to a method of treating a patient comprising identifying a patient suffering from overactive bladder, and administering to the patient a therapeutically effective amount of a first compound and a therapeutically effective amount of a second compound, wherein the first compound is an antimuscarinic or an anticholinergic agent, as described above, and second compound relieves constipation, as described above.

In some embodiments, the patient may be suffering from overactive bladder, urge, stress, and mixed incontinence.

In yet another aspect, the present invention relates to a method of treating a patient comprising administering to a patient in need thereof a therapeutically effective amount of a first compound, a therapeutically effective amount of a second compound, and a therapeutically effective amount of a third compound, wherein the first compound is an antimuscarinic or an anticholinergic agent, as described above, the second compound causes stimulation of salivary glands, as described above, and the third compound relieves constipation, as described above.

In some embodiments, the patient may be suffering from overactive bladder, urge, stress, and mixed incontinence.

In some embodiments in the above methods, the first compound and the second compound are administered more or less simultaneously. In other embodiments the first compound is administered prior to the second compound. In yet other embodiments, the first compound is administered subsequent to the second compound.

In certain embodiments in the above methods, the first compound and the second compound are administered individually. In other embodiments, the first compound and the second compound may be covalently linked to each other such that they form a single chemical entity. The single chemical entity is then digested and is metabolized into two separate physiologically active chemical entities, one of which is the first compound and the other one is the second compound. Both chemical entities once metabolized exert their therapeutic effect independently or synergistically. In further embodiments the bond between the two parts of the compound is not broken and each part of the joint molecule exerts its therapeutic effect independently, without the necessity of the cleavage of linker between the two parts.

It should be noted that simply taking commercially available pilocarpine HCl, e.g., Salagen® tablets, or any other salivary gland stimulants in conjunction with an OAB drug is not effective to alleviate the dry mouth side effect. Certain effective treatments match the pharmacokinetics profile of each salivary gland stimulants, such as pilocarpine, cevimeline HCl, and amifostine, with the pharmacokinetics profiles of the OAB agents, for example oxybutynin, tolterodine, solifenacin, darifenacin, trospium, and other approved agents or in development.

Therefore, in certain embodiments in the above methods, the first and second compounds are administered such that the peak plasma concentration for the first compound occurs at nearly the same time after administration as the peak plasma concentration for the second compound. Thus, the two compounds may be administered simultaneously, but be formulated such that the delay in their release causes the two peak plasma concentrations to occur at nearly the same time. In other embodiments, one compound is administered at a time interval after the other compound in order to ensure that the peak plasma concentrations occur at nearly the same time.

In other embodiments in the above methods, the first and second compounds are administered such that the time point at which the lowest saliva flow occurs because of the action of the first compound nearly corresponds to the time point at which the highest saliva flow occurs because of the action of the second compound. Thus, the two compounds may be administered simultaneously, but be formulated such that the delay in their release causes the peak saliva flow time point for the second compound to occur at nearly the same time as the lowest saliva flow time point for the first compound. In other embodiments, one compound is administered at a time interval after the other compound in order to ensure that peak and trough saliva flow time points match.

In some embodiments in the above methods, the first and second compounds are administered such that the ratio of their plasma concentrations, at a given point in point following their administration, is a predetermined value. Those of ordinary skill in the art recognize that the ratio of plasma concentrations is not necessarily the same as the ratio of the amount of compound administered. Compounds are digested differently in the gut, pass the gut wall differently, and have a different rate of first-pass metabolism in the liver. Furthermore, the clearance rate by the kidney is different for various compounds. Thus, for example, even if two compounds are administered in equivalent molar amounts, their plasma concentrations at a point in time after the administration may be significantly different. The methods disclosed herein take into account the pharmacokinetics of drug intake and metabolism, such that the ratio of the two compounds at the time of administration is adjusted so that the two compounds would have a predetermined concentration ratio in the plasma.

In yet other embodiments in the above methods, the first and second compounds are administered such that the time point for the maximum therapeutic effect of the compound that stimulates saliva flow matches the time point for the maximum side effect of the OAB therapeutic compound. Thus, the two compounds may be administered simultaneously, but be formulated such that the delay in their release causes the maximum therapeutic effect of the second compound to occur at nearly the same time as the maximum side effect of the first compound. In other embodiments, one compound is administered at a time interval after the other compound in order to ensure that the maximum therapeutic effect of the second compound to occur at nearly the same time as the maximum side effect of the first compound.

In some embodiments the dosage form is designed as sustained release of one agent combined with either sustained release or immediate release of the second agent to ensure that the peak plasma concentrations occur at nearly the same time. Further the dosage from can be designed based on the pharmacokinetics profiles where the peak plasma concentration of one compound, for example the salivary gland stimulant agent, e.g., pilocarpine, corresponds to maximum amount of mouth dryness caused by the OAB drug, for example oxybutynin.

Thus, some of the pharmaceutical compositions contemplated for use in the methods disclosed herein include, but are not limited to:

immediate release oxybutynin, tolterodine, solifenacin, darifenacin, trospium, or fesoterodine, in combination with pilocarpine and tegaserod;

delayed (whether sustained or extended) release oxybutynin and delayed (whether sustained or extended) release pilocarpine;

delayed (whether sustained or extended) release oxybutynin and delayed (whether sustained or extended) release pilocarpine and sustained release tegaserod;

immediate release oxybutynin, tolterodine, solifenacin, darifenacin, trospium, or fesoterodine, and delayed (whether sustained or extended) formulation of pilocarpine and tegaserod;

delayed (whether sustained or extended) release oxybutynin, tolterodine, solifenacin, darifenacin, trospium, or fesoterodine, and delayed (whether sustained or extended) release of pilocarpine and sustained release tegaserod;

delayed (whether sustained or extended) release oxybutynin, tolterodine, solifenacin, darifenacin, trospium, or fesoterodine, and delayed (whether sustained or extended) formulation of pilocarpine and immediate release formulation of tegaserod.

Without being bound by a particular theory, the improved treatment disclosed here of OAB in addressing the dry mouth and constipation is based on a mechanistic approach working at the receptor level, i.e., the adverse effect of these M2/M3 muscarinic antagonists is counteracted or negated with cholinergic agents that work in the opposite direction but in concert with the intended therapy.

Besides reducing the adverse side effects experienced by those being treated for overactive bladder, the methods and compositions disclosed herein have additional advantages. Currently, the dose of treatment drugs, such as oxybutynin, is limited because of the side effects. Some patients who suffer from overactive bladder cannot tolerate dosages that provide adequate therapy because of the adverse side effects, e.g., dry mouth. These patients continue to suffer from overactive bladder even though they take their medications, solely because the medication is not administered at an effective dose. By lowering the side effects using the methods and compositions disclosed herein, the patient can be prescribed to take treatment drugs, such as oxybutynin, at higher doses. These higher doses result in having a less active bladder and also result in an increase in intrinsic bladder capacity.

Thus, in another aspect, the present invention relates to a method of increasing intrinsic bladder capacity, comprising administering to a patient in need thereof a therapeutically effective amount of a first compound and a therapeutically effective amount of a second compound, wherein the first compound is an antimuscarinic or an anticholinergic agent, as described above, and the second compound causes stimulation of salivary glands, as described above.

In another aspect, the present invention relates to a method of increasing intrinsic bladder capacity, comprising administering to a patient in need thereof a therapeutically effective amount of a first compound and a therapeutically effective amount of a second compound, wherein the first compound is an antimuscarinic or an anticholinergic agent, as described above, and the second compound relieves constipation, as described above.

In another aspect, the present invention relates to a method of increasing intrinsic bladder capacity, comprising administering to a patient in need thereof a therapeutically effective amount of a first compound, a therapeutically effective amount of a second compound, and a therapeutically effective amount of a third compound, wherein the first compound is an antimuscarinic or an anticholinergic agent, as described above, the second compound causes stimulation of salivary glands, as described above, and the third compound relieves constipation, as described above.

In another aspect, the invention relates to a pharmaceutical composition comprising a combination of:

an antimuscarinic or an anticholinergic agent, as described herein, and a compound that causes stimulation of salivary glands, as described herein;

an antimuscarinic or an anticholinergic agent, as described herein, and a compound that relieves constipation, as described herein; or an antimuscarinic or an anticholinergic agent, as described herein, a compound that causes stimulation of salivary glands, as described herein, and a compound that relieves constipation, as described herein; and a physiologically acceptable carrier, diluent, or excipient, or a combination thereof.

The term "pharmaceutical composition" refers to a mixture of a compound of the invention with other chemical components, such as diluents, lubricants, bulking agents, desentegrant or carriers. The pharmaceutical composition facilitates administration of the compound to an organism. Multiple techniques of administering a compound exist in the art including, but not limited to, oral, injection, inhalation, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

In certain embodiments, the same substance can act as a carrier, diluent, or excipient, or have any of the two roles, or have all three roles. Thus, a single additive to the pharmaceutical composition can have multiple functions.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, transdermal, rectal, transmucosal, or intestinal administration; parenteral delivery, including intramuscular, subcutaneous, intravenous, intramedullary injections, as well as inhalation, intrathecal, direct intraventricular, intraperitoneal, intranasal, or intraocular injections.

Alternately, one may administer the compound in a local rather than systemic manner, for example, via injection of the compound directly in the renal or cardiac area, often in a depot or sustained, extended, or delayed release formulation. In addition, one may administer the composition by transdermal approach.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen and desired pharmacokinetics profiles of each component of combination therapy. Any of the well-known techniques, carriers, and excipients may be used as suitable and as understood in the art; e.g., in Remington's Pharmaceutical Sciences, above.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by mixing one or more solid excipient with pharmaceutical combination of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

The compounds may also be formulated in rectal compositions such as suppositories or retention enemas.

Many of the compounds used in the pharmaceutical combinations of the invention may be provided as salts with pharmaceutically compatible counterions. Pharmaceutically compatible salts may be formed with many acids, including but not limited to hydrochloric, sulfuric, acetic, lactic, tartaric, malic, succinic, and the like. Salts tend to be more soluble in aqueous or other protonic solvents than are the corresponding free acids or base forms.

Pharmaceutical compositions suitable for use in the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated.

Typically, the dose range of the composition administered to the patient can be from about 0.5 to 1000 mg/kg of the patient's body weight. The dosage may be a single one or a series of two or more given in the course of one or more days, as is needed by the patient. Note that for almost all of the specific compounds mentioned in the present disclosure, human dosages for treatment of at least some condition have been established. For example, for oxybutynin, tolterodine, solifenacin, darifenacin, trospium, fesoterodine the preferred dosage is between 0.1 mg to 50 mg, and the more preferred dosage is between 1 mg to 30 mg. Other dose ranges include between 10 to 50 mg, between 20 to 50 mg, between 30 to 50 mg, between 40 to 50 mg, between 20 to 40 mg, between 10 to 20 mg, between 10 to 30 mg, between 20 to 30 mg, and between 30 to 40 mg. The dose may also be at 10 mg, 20 mg, 30 mg, 40 mg, or 50 mg. For pilocarpine, the preferred dosage is between 0.1 mg to 50 mg, and the more preferred dosage is between 1 mg to 30 mg. Other dose ranges include between 10 to 50 mg, between 20 to 50 mg, between 30 to 50 mg, between 40 to 50 mg, between 20 to 40 mg, and between 30 to 40 mg. The dose may also be at 10 mg, 20 mg, 30 mg, 40 mg, or 50 mg. For tegaserod, the preferred dosage is between 0.05 mg to 50 mg, and the more preferred dosage is between 0.5 mg to 2 mg. Other dose ranges include between 10 to 50 mg, between 20 to 50 mg, between 30 to 50 mg, between 40 to 50 mg, between 20 to 40 mg, between 30 to 40 mg, between 0.5 to 1 mg, and between 1 to 2 mg. The dose may also be at 0.5 mg, 1 mg, 1.5 mg, and 2 mg.

Although the exact dosage can be determined on a drug-by-drug basis, in most cases, some generalizations regarding the dosage can be made. The daily dosage regimen for an adult human patient may be, for example, an oral dose of between 0.001 mg and 1000 mg of each ingredient, preferably between 0.01 mg and 500 mg, for example 1 to 200 mg or each ingredient of the pharmaceutical compositions of the present invention or a pharmaceutically acceptable salt thereof calculated as the free base or free acid, the composition being administered 1 to 4 times per day or per week. Alternatively the compositions of the invention may be administered by continuous such as sustained, delayed, or extended release, preferably at a dose of each ingredient up to 500 mg per day. Thus, the total daily dosage by oral administration of each ingredient will typically be in the range 0.1 mg to 2000 mg. Suitably the compounds will be administered for a period of continuous therapy, for example for a day, a week or more, or for months or years.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

It will be understood by those of skill in the art that numerous and various modifications can be made without departing from the spirit of the present invention. Therefore, it should be clearly understood that the forms of the present invention are illustrative only and are not intended to limit the scope of the present invention.

EXAMPLES

The examples below are non-limiting and are merely representative of various aspects of the invention.

Example 1

Combination of an OAB Drug and a Salivary Gland Stimulant for the Treatment of Individual with Overactive Bladder An individual with overactive bladder is identified. The individual is given 5 mg of oxybutynin two to four times a day in addition to 5 mg of pilocarpine two or three times a day. If the individual continues to complain about dry mouth, the dose of pilocarpine is increased to 10 mg two or three times a day. The dose can be increased up to 20 mg, or 50 mg, if needed. Each dose of oxybutynin can be increased to 10, 15, 20, or 30 mg.

Example 2

Combination of an OAB Drug and a Tegaserod for the Treatment of Individual with Overactive Bladder An individual with overactive bladder is identified. The individual is given 5 mg of oxybutynin two to four times a day in addition to 2 mg of tegaserod twice a day. If the individual continues to complain about constipation, the dose of tegaserod is increased to 6 mg twice a day. The dose can be increased up to 12 mg, 20 mg, or 50 mg, if needed. The dose of oxybutynin can be increased to 10, 15, 20, or 30 mg.

Example 3

Clinical Study Protocol Synopsis

A study is conducted to evaluate the effect of oxybutynin and pilocarpine, alone and in combination versus placebo on salivary output in healthy volunteers. The objectives of the study are to determine salivary flow and degree of dry mouth after oral administration of oxybutynin and pilocarpine, alone and in combination, vs. placebo, and to determine the effect of oxybutynin and pilocarpine, alone and in combination, on urine volume/void and vital signs.

At each treatment period, following an overnight fast, subjects enter the clinic and after baseline measurements have been made, they are randomized to one of four medications Oxybutynin (5 mg) followed 30 minutes later by placebo Pilocarpine (5 mg) followed 30 minutes later by placebo Placebo followed 30 minutes later by placebo Oxybutynin (5 mg) followed 30 minutes by pilocarpine (5 mg)

The following measurements are made just prior to and at frequent intervals for up to 6 hours post dose:

Salivary flow is determined by chewing Parafilm for 2 minutes

Dry mouth is determined by VAS

Urine volume/void and frequency over 6 hours post dose is measured

Blood samples are taken for pharmacokinetics at pre-dose, and at 0.5, 1, 2, 3, 4, and 6 hours post dose Food and water intake are standardized over the 6 hour period The study is a double blind, randomized, placebo-controlled, with 4 sequences (4 doses over 4 weeks) with the drugs being administered orally as a single dose. There is a One-week washout between study days. The study population is chosen as follows:

Healthy volunteers 12 subjects

≧18 years males or non-pregnant females

Weight 18-28 BMI

No known allergy to antimuscarinic agents

No previous history of glaucoma, urinary retention, cardiac arrhythmias

No OTC medications, nutriceuticals or vitamins within 10 days of study enrollment and throughout the study Assessments (except for urine output) is performed at: 0.5 hr and within 10 minutes pre-dose, 0.5, 1, 1.5, 2, 2.5, 3, 3.5, 4, 4.5, 5, and 6 hours post dose. The following are assessed:

1) Stimulated salivary flow
2) Dry mouth (VAS)
3) Urine volume/void over 6 hours post dose
4) Pharmacokinetics of oxybutynin and pilocarpine The standard safety precautions, such as physical exam, medical history, con-meds, ECG, hematology, clinical chemistry, urinalysis performed at screening and study termination, urine drug/alcohol screening at pre-dose for each period, vital signs (HR and BP) at: pre-dose, and at 30 min intervals for 6 hours, and an awareness of adverse events throughout and between study period, are taken.

Example 4

Case Study for a Combination of Oxybutynin and Pilocarpine

In this study, the effect of oxybutynin, pilocarpine, the combination of the two, and placebo was measured in six separate, yet identical, studies in a single individual.

Effect of Oxybutynin—A healthy human subject was given a 5 mg dose of oxybutynin HCl and the amount of salivation was measured with time over an 8 hour period. As shown in FIG. 1 (♦, diamond), the amount of saliva flow collected over 2 minutes periods decreased after dosing of oxybutynin and the saliva flow remained low after 3 hrs. The amount of saliva flow started increasing after 3 hrs and continued increasing reaching the pre-dose level after 8 hrs post-dosing. The data generated in this study is consistent with the literature data.

Effect of Pilocarpine—In a separate human study the effect of pilocarpine HCl was evaluated in a healthy human subject to ensure that pilocarpine indeed increases salivary gland flow. This was demonstrated as shown in FIG. 1 (■, square). The amount of saliva collected over 2 minute periods increased sharply after dosing and the saliva flow started decreasing after the peak observed at half an hour. The decrease in saliva flow continued until it reached about the normal saliva flow and pre-dosing level after about 5 hrs.

Effect of Placebo—In the third leg of the human study, the effect of placebo was evaluated. Since this was an unblinded trial, the salivary flow was measured by not taking any medication or a true placebo but the same protocol was followed as in the other studies. As shown in the FIG. 1 (▲, triangle), the variation in salivary flow with time is minimal and the average salivary flow is about 2 g/2 min, consistent with the published literature.

Effect of Combination of Oxybutynin and Pilocarpine—In a separate human study, the combination of oxybutynin and pilocarpine was administered to a healthy human subject. To the subject 5 mg of oxybutynin followed by 5 mg of pilocarpine after 30 min of dosing was administered. Saliva flow was measured as before. Results are shown in FIG. 1 (●, circle).

As shown in FIG. 1, the decreased in salivary flow caused by oxybutynin was compensated well by the increase in salivary flow induced by pilocarpine. As a result, the amount of salivary flow remained about the same as the pre-dose level. FIG. 1 further shows that the amount of salivary flow measured for the combination study was similar to that of the placebo study. Therefore, administration of 5 mg pilocarpine at half hour after the administration of 5 mg of oxybutynin completely neutralized the adverse side effect of oxybutynin.

Figure 2:
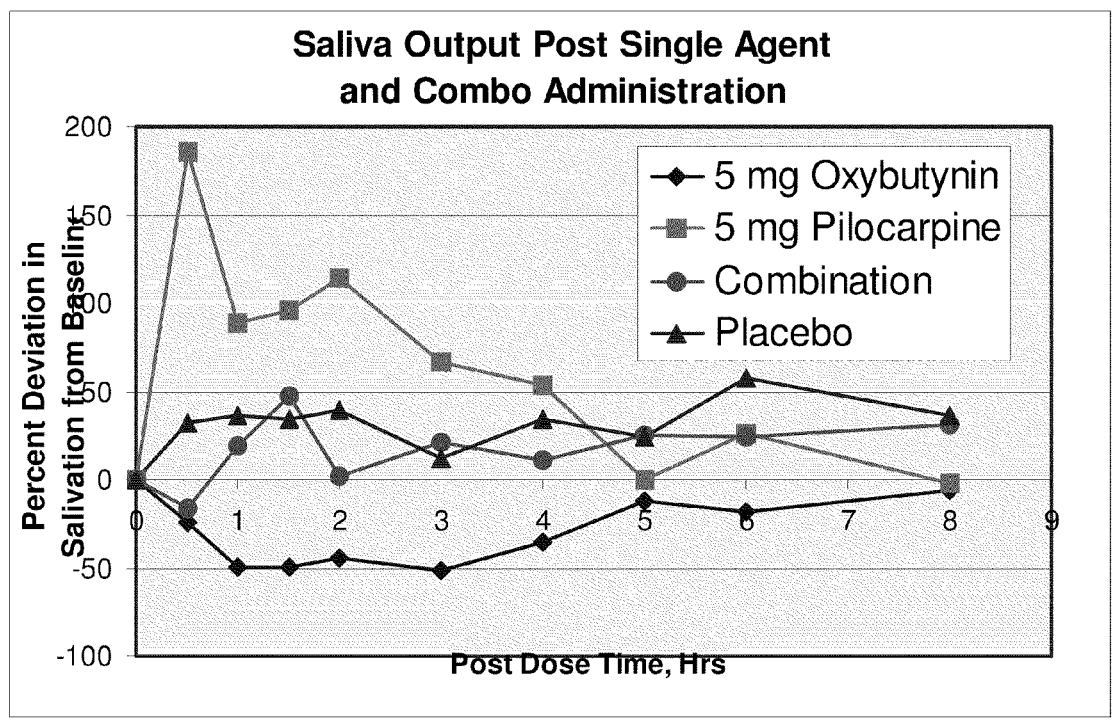
FIG. 2 is a graph showing the percentage of saliva flow with reference to time zero.

The percentage of saliva flow deviation from baseline following administration of pilocarpine, oxybutynin, combination of pilocarpine and oxybutynin (with pilocarpine administered 30 min after oxybutynin), and placebo were plotted against time and are shown in FIG. 2. The percent deviation for the combination study, where pilocarpine was administered 30 min after oxybutynin, (●, circle) is minimal and not significantly different from the baseline or the placebo (▲, triangle) suggesting that the combination approach eliminates the major side effect of OAB therapy.

Figure 3:
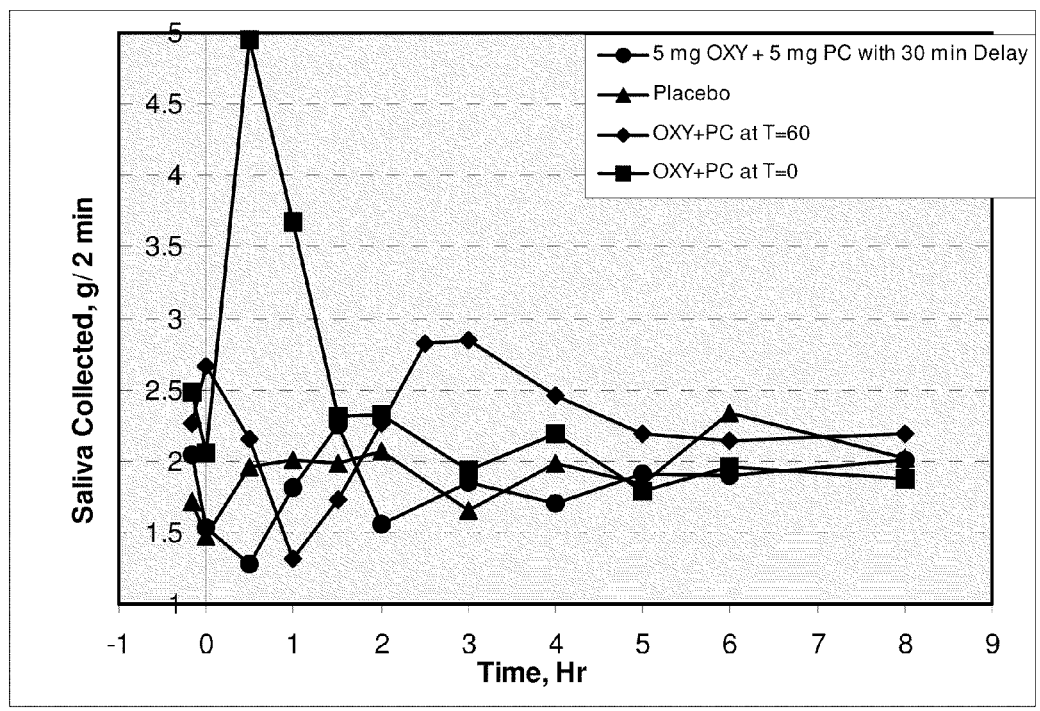
FIG. 3 is a graph showing the effect of time delay for the administration of pilocarpine, with oxybutynin being administered at t=0 for all experiments, except for placebo (▲, triangle) where there was no oxybutyin, and pilocarpine being administered at t=0 (■, square), t=30 min (●, circle), and t=60 min (♦, diamond).

Effect of Timing of the Administration of Pilocarpine with Respect to the Administration of Oxybutynin—In two additional human studies, the effect of the timing of administration of pilocarpine was measured. In one study, the combination of oxybutynin and pilocarpine was administered to a healthy human subject. To the subject 5 mg of oxybutynin and 5 mg of pilocarpine were administered simultaneously. Saliva flow was measured as before. Results are shown in FIG. 3 (■, square). In the last study, the combination of oxybutynin and pilocarpine was administered to a healthy human subject. To the subject 5 mg of oxybutynin followed by 5 mg of pilocarpine after 60 min of dosing was administered. Saliva flow was measured as before. Results are shown in FIG. 3 (♦, diamond).

FIG. 3 shows the effect of time delay for the administration of pilocarpine. All studies are compared to placebo (▲, triangle). When oxybutynin and pilocarpine are administered at the same time (■, square), there is an initial large increase in saliva flow, which reaches a maximum at about t=30 min to less than about t=60 min, but then drops to normal (placebo) levels at about t=1 hr and stays at this level. When pilocarpine is administered 60 minutes after oxybutynin (♦, diamond), there is a precipitous drop in saliva flow which last until about t=1 hr, after which there is a large increase in saliva flow, with a maximum occurring at about t=3 hrs. The saliva flow returns to normal (placebo) at about t=5 hrs. However, when pilocarpine is administered 30 minutes after oxybutynin (●, circle), there is a small drop in saliva flow with a minimum at about t=30 min, but it returns to normal (placebo) within one hour.

Figure 4:
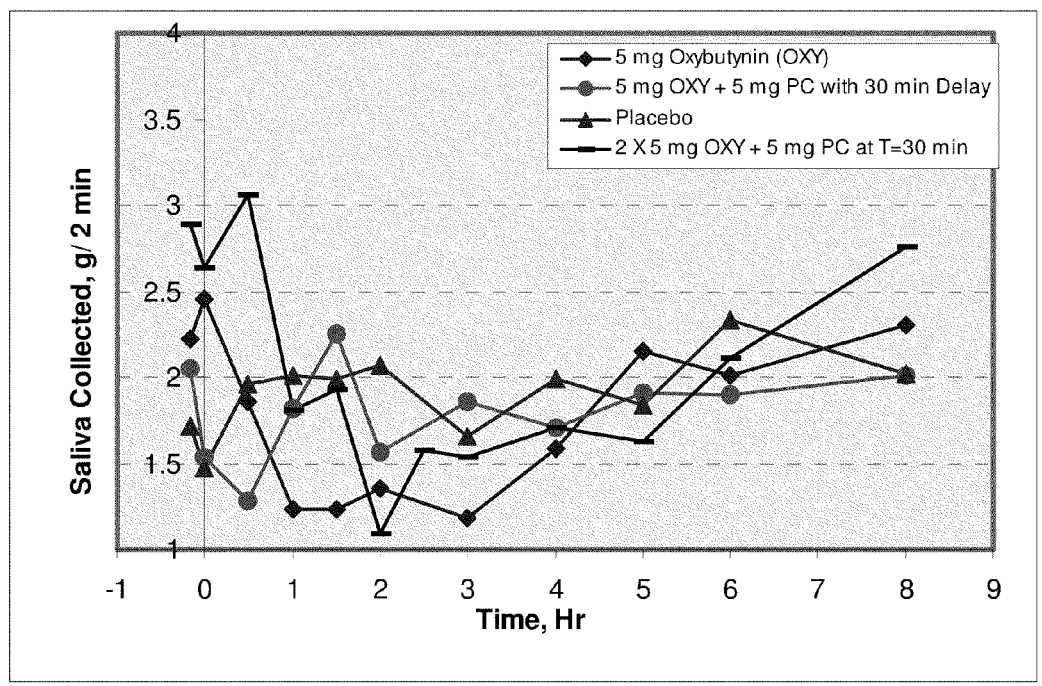
FIG. 4 is a graph showing the effect of different dose ratios between oxybutynin and pilocarpine on saliva flow.

Effect of Dose Ratio Between Oxybutynin and Pilocarpine—In this experiment the results of two separate dose ratios between oxybutynin and pilocarpine were compared with the results of placebo and administration of oxybutynin alone. In one experiment, 5 mg of oxybutynin was administered to a healthy individual and saliva flow was measured for 8 hours. The results are shown in FIG. 4 (♦, diamond). Using a similar protocol, 5 mg of oxybutynin was administered to a healthy individual at t=0, followed by 5 mg of pilocarpine at t=30 min. The results are shown in FIG. 4 (●, circle). Similarly, 10 mg of oxybutynin was administered to a healthy individual at t=0, followed by 5 mg of pilocarpine at t=30 min. The results are shown in FIG. 4 (-, dash). Finally, the results were compared with the administration of placebo (FIG. 4 (▲, triangle)).

The results shown in FIG. 4 suggest that increasing oxybutynin from 5 to 10 mg lead to decrease in salivation. The increase in ratio from 1:1 to 2:1 perturbs the balance between the decreased salivation by oxybutynin and increased salivation by pilocarpine, respectively. It is noted that the saliva flow for the 2:1 oxybutynin:pilocarpine ratio is similar to that of the 5 mg oxybutynin alone, suggesting that the amount of 5 mg pilocarpine in this experiment is not sufficient to compensate the decrease in saliva flow caused by the increase in amount of oxybutynin from 5 to 10 mg. Therefore, an effective dose ratio for the combination oxybutynin and pilocarpine is when 5 mg of each is administered to a patient.

Plasma Concentration of Oxybutynin—a separate study, the plasma concentration of oxybutynin was measured in two groups of subjects: one group received 5 mg of oxybutynin alone and another group received 5 mg of oxybutynin followed by 5 mg pilocarpine after 30 min. The plasma concentrations were measured before the administration of oxybutynin and in hours 1, 2, 3, 4, and 6 after its administration. The results are shown in Tables 1 and 2, below. Table 1 shows the plasma levels of oxybutynin after the administration of 5 mg of oxybutynin alone in a placebo controlled, blinded, four way crossover clinical trial in 12 male subjects. Table 2 presents the plasma levels of oxybutynin after the administration of 5 mg of oxybutynin followed by the administration of 5 mg of pilocarpine 30 min after the administration of oxybutynin in a placebo controlled, blinded, four way crossover clinical trial in 12 male subjects.

TABLE 1

| Subject | Plasma Level of Oxybutynin (ng/mL) Time (Hour) After Oxybutynin Administration | | | | | |
|---|---|---|---|---|---|---|
| Number | 0 | 1 | 2 | 3 | 4 | 6 |
| 1 | 0.000 | 0.980 | 1.760 | 1.620 | 0.869 | 0.786 |
| 2 | 0.000 | 5.380 | 2.910 | 2.410 | 1.490 | 1.150 |
| 3 | 0.000 | 9.840 | 3.870 | 2.320 | 1.840 | 1.150 |
| 4 | 0.120 | 3.250 | 1.990 | 1.270 | 1.070 | 0.783 |
| 5 | 0.020 | 16.000 | 9.260 | 3.920 | 4.690 | 1.900 |
| 6 | 0.000 | 2.600 | 1.400 | 1.230 | 1.140 | 1.330 |
| 7 | 0.000 | 15.420 | 6.110 | 2.700 | 2.390 | 0.650 |
| 8 | 0.000 | 7.600 | 2.890 | 1.530 | 0.010 | 0.000 |
| 9 | 0.000 | 3.910 | 2.580 | 0.440 | 0.210 | 0.190 |
| 10 | 0.000 | 7.230 | 3.120 | 1.330 | 0.880 | 0.190 |
| 11 | 0.000 | 4.900 | 1.820 | 0.970 | 0.340 | 0.560 |
| 12 | 0.000 | 3.200 | 1.520 | 0.790 | 0.230 | 0.000 |
| Mean | 0.012 | 6.693 | 3.269 | 1.711 | 1.263 | 0.724 |
| STD | 0.034597 | 4.861029 | 2.289476 | 0.969634 | 1.291618 | 0.585548 |

TABLE 2

| Subject | Plasma Level of Oxybutynin (ng/mL) Time (Hour) After Oxybutynin Administration | | | | | |
|---|---|---|---|---|---|---|
| Number | 0 | 1 | 2 | 3 | 4 | 6 |
| 1 | 0.000 | 1.830 | 1.380 | 0.980 | 0.977 | 0.740 |
| 2 | 0.000 | 5.260 | 2.490 | 1.220 | 1.820 | 1.100 |
| 3 | 0.000 | 1.720 | 2.120 | 6.920 | 5.150 | 3.100 |
| 4 | 0.020 | 3.080 | 2.790 | 2.230 | 1.460 | 0.150 |
| 5 | 0.000 | 14.600 | 6.580 | 2.550 | 5.010 | 1.580 |
| 6 | 0.000 | 2.750 | 1.690 | 1.280 | 1.020 | 0.000 |
| 7 | 0.000 | 20.800 | 11.100 | 5.310 | 3.060 | 2.110 |
| 8 | 0.000 | 1.180 | 0.470 | 0.230 | 0.270 | 0.000 |
| 9 | 0.000 | 8.580 | 2.920 | 1.410 | 0.940 | 0.550 |
| 10 | 0.000 | 9.200 | 3.650 | 1.870 | 1.110 | 0.340 |
| 11 | 0.000 | 7.490 | 1.710 | 1.340 | 0.600 | 0.680 |
| 12 | 0.000 | 3.480 | 1.520 | 0.930 | 0.560 | 0.260 |
| Mean | 0.001538 | 6.228462 | 3.109231 | 2.251538 | 1.998231 | 1.277692 |
| STD | 0 | 5.967714 | 2.92391 | 1.961773 | 1.67978 | 0.948956 |

As can be seen from the tables, in both groups, the plasma concentration of oxybutynin reaches a maximum at about an hour, followed by a gradual decline. Moreover, the plasma concentration of oxybutynin follows the same curve for both groups. Therefore, addition of 5 mg of pilocarpine does not affect the plasma concentration of oxybutynin at all. Two conclusions follow from this observation. First, pilocarpine does not affect the absorption of oxybutynin in the gut, nor does it affect the first-pass metabolism of pilocarpine in the liver. Second, pilocarpine does not affect the binding ability of oxybutynin, since the concentration of free oxybutynin in the plasma remains the same between the two groups. Further, the presence of pilocarpine in the combination does not interfere with the pharmacokinetics of oxybutynin. Thus, the antimuscarinic activity of oxybutynin responsible for therapeutic effect of oxybutynin on OAB remains unaffected.

Example 5

Case Study for a Combination of Oxybutynin and Cevimeline

In this study, the effect of oxybutynin, cevimeline, the combination of the two, and placebo was measured in separate studies in a single individual.

Figure 5:
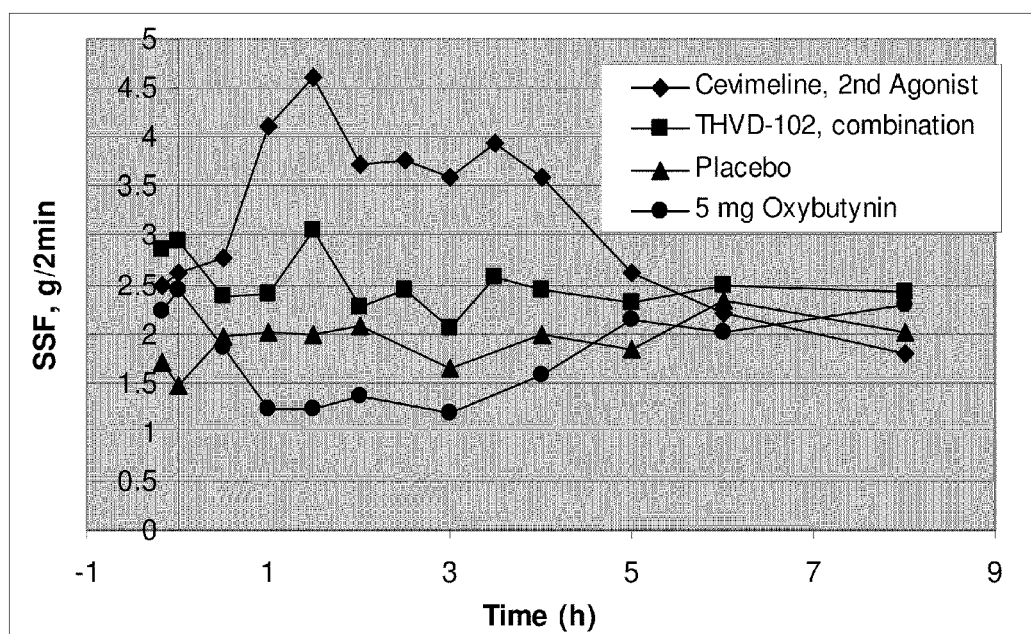
FIG. 5 is a graph showing the comparison of stimulated salivary output following oral administration of 5 mg oxybutynin (●, circle), 30 mg cevimeline (♦, diamond), placebo (▲, triangle), and a combination of oxybutynin and cevimeline (THVD-102) (■, square).

Effect of Oxybutynin—A healthy human subject was given a 5 mg dose of oxybutynin HCl and the amount of salivation was measured with time over an 8 hour period. As shown in FIG. 5 (●, circle), the amount of saliva flow collected over 2 minutes periods decreased after dosing and the saliva flow remained low after 3 hrs. The amount of saliva flow started increasing after 3 hrs and continued increasing reaching the pre-dose level after 8 hrs post-dosing. The data generated in this study is consistent with the literature data.

Effect of Cevimeline—In a separate human study the effect of administering 30 mg of cevimeline was evaluated in a healthy human subject to ensure that cevimeline indeed increases salivary gland flow. This was demonstrated as shown in FIG. 5 (♦, diamond). The amount of saliva collected over 2 minute periods increased sharply after dosing and the saliva flow started decreasing after the peak observed at close to two hours. The decrease in saliva flow continued until it reached about the normal saliva flow and pre-dosing level after about 6 hrs.

Effect of Placebo—In the third leg of the human study, the effect of placebo was evaluated. Since this was an unblinded trial, the salivary flow was measured by not taking any medication or a true placebo but the same protocol was followed as in the other studies. As shown in the FIG. 5 (▲, triangle), the variation in salivary flow with time is minimal and the average salivary flow is about 2.5 g/2 min, consistent with the published literature.

Effect of Combination of Oxybutynin and Cevimeline—In a separate human study, the combination of oxybutynin and cevimeline was administered to a healthy human subject. To the subject 5 mg of oxybutynin followed simultaneously by 30 mg of cevimeline, with no time delay, was administered. Saliva flow was measured as before. Results are shown in FIG. 5 (■, square), where the combination is referred to as THVD-102.

The results of the above experiments are also shown in the Table 3, below, which shows the data for the evaluation of the combination of oxybutynin and cevimeline on stimulated salivary flow. FIG. 5 is a graphic illustration of the data set forth in Table 3.

TABLE 3

| Agent | Cevimeline | Cev + Oxy | Oxybutynin | Placebo |
|---|---|---|---|---|
| Oxybutynin, mg | 0 | 5 | 5 | 0 |
| Cevimeline, mg | 30 | 30 | 0 | 0 |

| Time (hr) | Amount of Saliva Collecetd over 2 min | | Amount of Saliva Collecetd over 2 min | |
|---|---|---|---|---|
| −0.17 | 2.4808 | 2.862 | 2.2208 | 1.7143 |
| 0 | 2.6273 | 2.9442 | 2.4536 | 1.4786 |
| 0.5 | 2.7791 | 2.3742 | 1.8558 | 1.959 |
| 1 | 4.1213 | 2.4091 | 1.2308 | 2.0143 |
| 1.5 | 4.6029 | 3.0437 | 1.2326 | 1.9861 |
| 2 | 3.7314 | 2.2793 | 1.3548 | 2.0671 |
| 2.5 | 3.7641 | 2.4445 | n/d* | n/d |
| 3 | 3.5888 | 2.0601 | 1.1829 | 1.6538 |
| 3.5 | 3.9316 | 2.5827 | n/d | n/d |
| 4 | 3.5914 | 2.4358 | 1.5868 | 1.9866 |
| 5 | 2.6099 | 2.312 | 2.1475 | 1.8417 |
| 6 | 2.205 | 2.4915 | 2.0096 | 2.3332 |
| 8 | 1.7973 | 2.4158 | 2.3028 | 2.0182 |

*Not determined

As shown in FIG. 5, the decreased in salivary flow caused by oxybutynin was compensated well by the increase in salivary flow induced by cevimeline. As a result, the amount of salivary flow remained about the same as the pre-dose level. FIG. 5 further shows that the amount of salivary flow measured for the combination study was similar to that of the placebo study. Therefore, administration of 30 mg cevimeline simultaneously with the administration of 5 mg of oxybutynin completely neutralized the adverse side effect of oxybutynin.

Example 6

Case Study for a Combination of Tolterodine and Pilocarpine

In this study, the effect of tolterodine, pilocarpine, the combination of the two, and placebo was measured in separate, yet identical, studies in a single individual.

Figure 6:
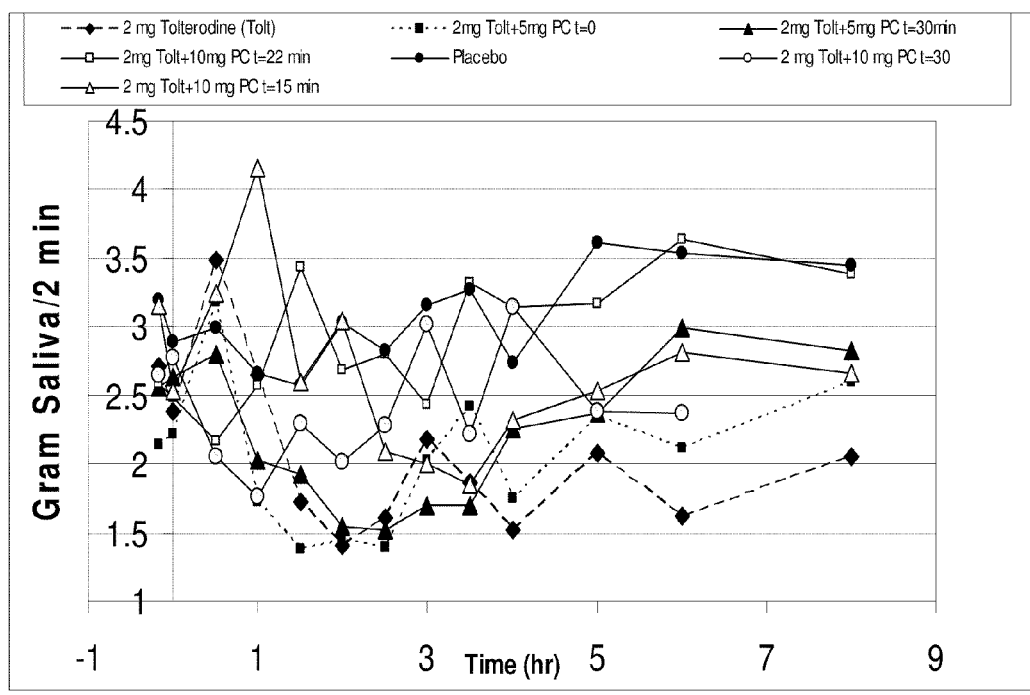
FIG. 6 is a graph showing the comparison of stimulated salivary output following oral administration of 2 mg tolterodine tartrate, with various combinations (2 mg tolterodine/5 mg pilocarpine and 2 mg tolterodine/10 mg pilocarpine with pilocarpine administered at different times), and placebo.
Figure 7:
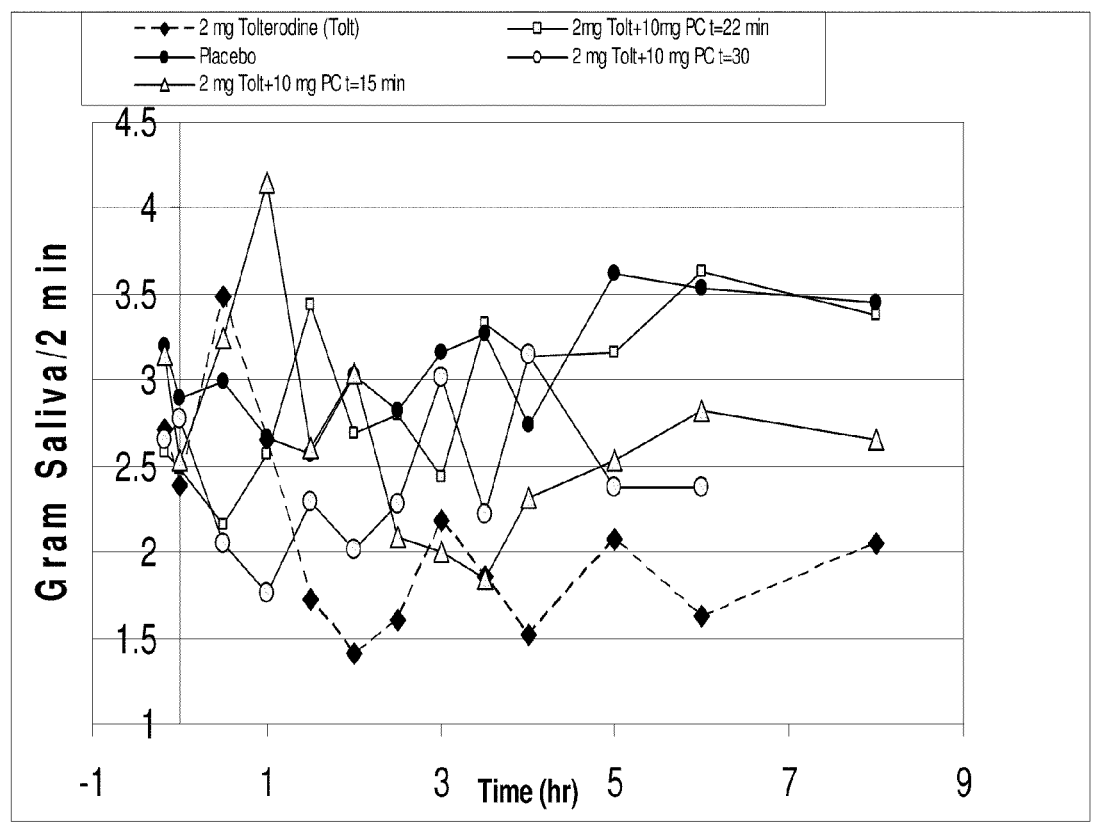
FIG. 7 is a graph showing the relationship of time of administration of 10 mg of pilocarpine on stimulated salivary output after oral administration of 2 mg tolterodine tartrate.

Effect of Tolterodine—A healthy human subject was given a 2 mg dose of tolterodine tartrate and the amount of salivation was measured with time over an 8 hour period. As shown in FIGS. 6 and 7 (♦, diamond), the amount of saliva flow collected over 2 minute periods decreased after dosing and the saliva flow remained low after 3 hrs. The amount of saliva flow started increasing after about 4 hrs and continued increasing, but did not completely reach the pre-dose levels even after 8 hrs post-dosing.

Effect of Pilocarpine—The effect of the administration of pilocarpine individually has been studied and the data is shown above.

Effect of Placebo—In another leg of the human study, the effect of placebo was evaluated. Since this was an unblinded trial, the salivary flow was measured by not taking any medication or a true placebo but the same protocol was followed as in the other studies. As shown in the FIGS. 6 and 7 (●, closed circle), the variation in salivary flow with time is minimal and the average salivary flow is about 2.5 g/2 min, consistent with the published literature.

Effect of Dose Ratio Between Tolterodine and Pilocarpine—In this experiment the results of two separate dose ratios between tolterodine and pilocarpine were compared with the results of placebo and administration of tolterodine alone. In one experiment, 2 mg of tolterodine was administered to a healthy individual and saliva flow was measured for 8 hours. The results are shown in FIG. 6 (♦, diamond). Using a similar protocol, 2 mg of tolterodine was administered to a healthy individual at t=0, followed by 5 mg of pilocarpine at t=30 min. The results are shown in FIG. 6 (▲, closed triangle). Similarly, 2 mg of tolterodine was administered to a healthy individual at t=0, followed by 10 mg of pilocarpine at t=30 min. The results are shown in FIG. 6 (○, open circle). Finally, the results were compared with the administration of placebo (FIG. 6 (●, closed circle)). The results shown in FIG. 6 suggest that increasing pilocarpine from 5 to 10 mg lead to increase in salivation. The decrease in ratio from 2:5 to 2:10 (tolterodine:pilocarpine) restores the balance between the decreased salivation by tolterodine and increased salivation by pilocarpine, respectively. It is noted that the saliva flow for the 2:5 tolterodine:pilocarpine ratio is similar to that of the 2 mg tolterodine alone, suggesting that the amount of 5 mg pilocarpine in this experiment is not sufficient to compensate the decrease in saliva flow caused by 2 mg of tolterodine. Therefore, an effective dose ratio for the combination oxybutynin and pilocarpine is when 2 mg of tolterodine is combined with 10 mg of pilocarpine.

Effect of Combination of Tolterodine and Pilocarpine—In a separate human study, the combination of tolterodine and pilocarpine was administered to a healthy human subject. To the subject 2 mg of tolterodine followed by 10 mg of pilocarpine were administered with various delays in the administration of pilocarpine. Saliva flow was measured as before. Results are shown in FIG. 7.

In one study, 10 mg of pilocarpine was administered to the subject 15 minutes after the administration of 2 mg of tolterodine. Saliva flow was measured as before. Results are shown in FIG. 7 (Δ, open triangle). In another study, 10 mg of pilocarpine was administered to the subject 22 minutes after the administration of 2 mg of tolterodine. Saliva flow was measured as before. Results are shown in FIG. 7 (□, open square). In the last study, 10 mg of pilocarpine was administered to the subject 30 minutes after the administration of 2 mg of tolterodine. Saliva flow was measured as before. Results are shown in FIG. 7 (○, open circle).

As shown in FIG. 7, the decreased in salivary flow caused by tolterodine was compensated well by the increase in salivary flow induced by pilocarpine. As a result, the amount of salivary flow remained about the same as the pre-dose level, when pilocarpine was administered 22 minutes after the administration of tolterodine. FIG. 7 further shows that the amount of salivary flow measured for the combination study, with a 22 min delay for pilocarpine, was similar to that of the placebo study. Therefore, administration of 10 mg pilocarpine at 22 minutes after the administration of 2 mg of tolterodine completely neutralized the adverse side effect of oxybutynin.

Considering that the high doses are not tolerated because of the severity of the dry mouth, the disclosed approach allows administration of higher doses of oxybutynin, tolterodine, solifenacin, darifenacin, trospium, fesoterodine, and other approved or compounds in development, thus leading to a more tolerable, effective, and economical treatment.

What is claimed is:

1. A pharmaceutical composition comprising a therapeutically effective amount of oxybutynin or tolterodine, or a free base thereof or a pharmaceutically acceptable salt thereof, and pilocarpine, or a free base thereof or a pharmaceutically acceptable salt thereof; wherein the oxybutynin, or a free base thereof or a pharmaceutically acceptable salt thereof, is present in a dose of between 1 mg to 30 mg,
   wherein the tolterodine, or a free base thereof or a pharmaceutically acceptable salt thereof, is present in a dose of between 0.1 mg to 50 mg and
   wherein the pilocarpine, or a free base thereof or a pharmaceutically acceptable salt thereof, is present in a dose of between 1 mg to 30 mg.

2. The pharmaceutical composition of claim 1, further comprising a pharmaceutically acceptable carrier, diluent, or excipient.

3. The pharmaceutical composition of claim 1, wherein the oxybutynin, or a free base thereof or a pharmaceutically acceptable salt thereof, is present in a dose of 5 mg or in a dose of 10 mg.

4. The pharmaceutical composition of claim 1, wherein the tolterodine, or a free base thereof or a pharmaceutically acceptable salt thereof, is present in a dose of between 1 mg to 30 mg.

5. The pharmaceutical composition of claim 1, wherein the tolterodine, or a free base thereof or a pharmaceutically acceptable salt thereof, is present in a dose of 1 mg or in a dose of 2 mg.

6. The pharmaceutical composition of claim 1, wherein the pilocarpine, or a free base thereof or a pharmaceutically acceptable salt thereof, is present in a dose of 5 mg or in a dose of 10 mg.

7. The pharmaceutical composition of claim 2, wherein the excipient is selected from the group consisting of lactose, sucrose, mannitol, sorbitol, maize starch, wheat starch, rice starch, potato starch, gelatin, gum tragacanth, methyl cellulose, hydroxypropylmethyl cellulose, sodium carboxymethylcellulose, polyvinylpyrrolidone, sodium alginate, propylene glycol, and talc.

8. A method of treating overactive bladder in a patient comprising
   administering to a patient in need thereof a therapeutically effective amount of the pharmaceutical composition of claim 1.

9. The method of claim 8, wherein the oxybutynin, or a free base thereof or a pharmaceutically acceptable salt thereof, is present in a dose of 5 mg or in a dose of 10 mg.

10. The method of claim 8, wherein the tolterodine, or a free base thereof or a pharmaceutically acceptable salt thereof, is present in a dose of 1 mg or in a dose of 2 mg.

11. The method of claim 8, wherein the pilocarpine, or a free base thereof or a pharmaceutically acceptable salt thereof, is present in a dose of 5 mg or in a dose of 10 mg.

* * * * *